(12) United States Patent
Martins et al.

(10) Patent No.: US 9,156,747 B2
(45) Date of Patent: *Oct. 13, 2015

(54) ALKYLATION PROCESS USING PHOSPHONIUM-BASED IONIC LIQUIDS

(71) Applicant: UOP LLC, Des Plaines, IL (US)

(72) Inventors: Susie C. Martins, Carol Stream, IL (US); Douglas A. Nafis, Mount Prospect, IL (US); Alakananda Bhattacharyya, Glen Ellyn, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/796,776

(22) Filed: Mar. 12, 2013

(65) Prior Publication Data

US 2013/0345483 A1    Dec. 26, 2013

Related U.S. Application Data

(60) Provisional application No. 61/664,405, filed on Jun. 26, 2012.

(51) Int. Cl.
| | |
|---|---|
| *C07C 2/56* | (2006.01) |
| *C07C 2/58* | (2006.01) |
| *C07C 2/60* | (2006.01) |
| *C07C 2/62* | (2006.01) |

(52) U.S. Cl.
CPC .................................... *C07C 2/56* (2013.01)

(58) Field of Classification Search
CPC .............................................. C07C 2/56
USPC ............................................ 585/722
See application file for complete search history.

(56) References Cited

U.S. PATENT DOCUMENTS

| | | | |
|---|---|---|---|
| 7,198,712 | B2 | 4/2007 | Olivier-Bourbigou et al. |
| 7,569,740 | B2 * | 8/2009 | Elomari ................ 585/722 |
| 2005/0059848 | A1 * | 3/2005 | Randolph et al. ........ 585/723 |
| 2011/0233113 | A1 | 9/2011 | Koseoglu et al. |
| 2013/0345482 | A1 | 12/2013 | Martins |
| 2013/0345484 | A1 | 12/2013 | Martins |

OTHER PUBLICATIONS

Fraser et al., Phosphonium-Based Ionic Liquids: An Overview; Australian Journal of Chemistry 2009, 62 (4), pp. 309-321.

* cited by examiner

*Primary Examiner* — In Suk Bullock
*Assistant Examiner* — Youngsul Jeong

(57) ABSTRACT

A process for making an alkylate is presented. The process includes mixing an isoparaffin stream with an olefin stream in an alkylation reactor. The alkylation reactor includes a catalyst for performing the reaction. The catalyst is an ionic liquid that is a quaternary phosphonium based ionic liquid, and the reaction is performed at or near ambient temperatures.

20 Claims, 4 Drawing Sheets

ALKYLATION PROCESS USING PHOSPHONIUM-BASED IONIC LIQUIDS

CROSS-REFERENCE TO RELATED APPLICATION

This application claims the benefit of U.S. Provisional Application No. 61/664,405 filed on Jun. 26, 2012.

FIELD OF THE INVENTION

This invention relates to processes for the alkylation of paraffins. In particular, the use of ionic liquids for olefin-paraffin alkylation.

BACKGROUND OF THE INVENTION

The alkylation of paraffins with olefins for the production of alkylate for gasolines can use a variety of catalysts. The choice of catalyst depends on the end product a producer desires. Ionic liquids are catalysts that can be used in a variety of catalytic reactions, including the alkylation of paraffins with olefins. Ionic liquids are primarily mixtures of salts which melt below room temperature, and will form liquid compositions at a temperature below the individual melting points of the constituents.

Ionic liquids are essentially salts in a liquid state, and are described in U.S. Pat. Nos. 4,764,440, 5,104,840, and 5,824,832. The properties vary extensively for different ionic liquids, and the use of ionic liquids depends on the properties of a given ionic liquid. Depending on the organic cation of the ionic liquid and the anion, the ionic liquid can have very different properties. The behavior varies considerably for different temperature ranges, and it is preferred to find ionic liquids that do not require operation under more extreme conditions such as refrigeration.

SUMMARY OF THE INVENTION

The present invention is a process for the alkylation of isoparaffins. An isoparaffin stream and an olefin stream are passed to an alkylation reactor. The alkylation reactor includes a catalyst that is a phosphonium based ionic liquid, and includes a Brønsted acid co-catalyst. The reaction is carried out at a temperature greater than 0° C., and preferably carried out at a temperature greater than 20° C.

In one embodiment, the preferred ionic liquid is selected from the group consisting of tri-n-butyl-hexylphosphonium-$Al_2X_7$, trihexyl-tetradecylphosphonium-$Al_2X_7$, tripropyl-hexylphosphonium-$Al_2X_7$, tributylmethylphosphonium-$Al_2X_7$, tributylpentylphosphonium-$Al_2X_7$, tributyloctyl-phosphonium-$Al_2X_7$, tributyldecylphosphonium-$Al_2X_7$, tributyldodecylphosphonium-$Al_2X_7$, tributyltetradecylphosphonium-$Al_2X_7$, and mixtures thereof X comprises a halogen ion selected from the group consisting of F, Cl, Br, I, and mixtures thereof. The Brønsted acid is selected from the group consisting of HF, HCl, HBr, HI, and mixtures thereof.

The paraffins are selected from hydrocarbons having from 2 to 10 carbon atoms, with a preferred isoparaffin stream having 4 to 8 carbon atoms. The olefins are selected from olefins having from 2 to 10 carbon atoms, with a preferred olefin stream comprising 3 to 8 carbon atoms.

Other objects, advantages and applications of the present invention will become apparent to those skilled in the art from the following detailed description and drawings.

DETAILED DESCRIPTION OF THE INVENTION

Figure 1:
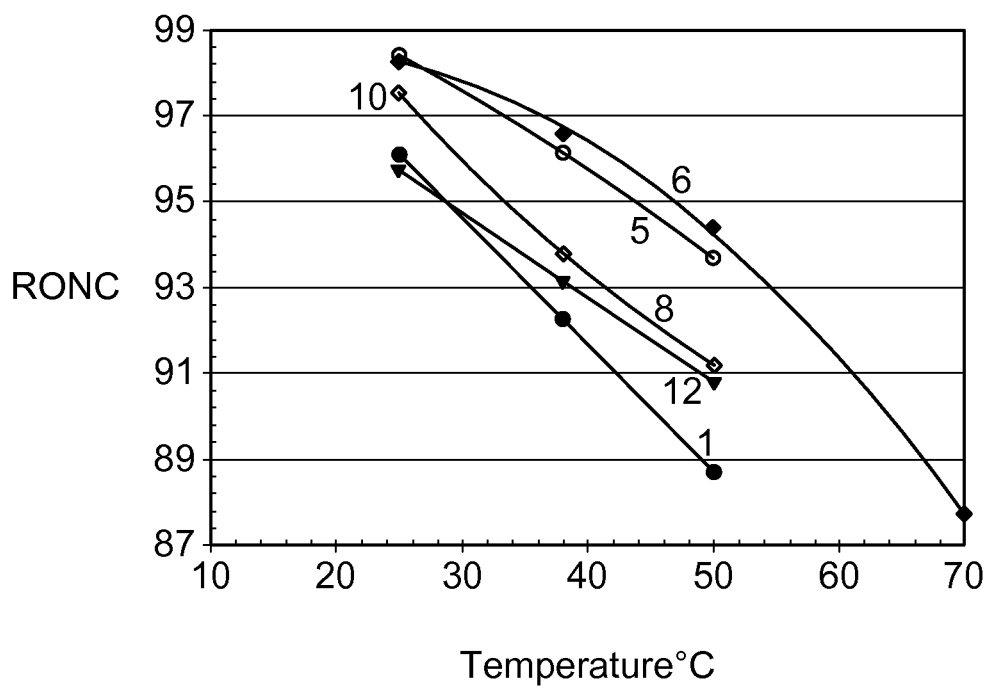
FIG. 1 shows the effect of asymmetric side chain length on alkylation performance of phosphonium chloroaluminate ionic liquids.

Ionic liquids have been presented in the literature, and in patents. Ionic liquids can be used for a variety of catalytic reactions, and it is of particular interest to use ionic liquids in alkylation reactions. Ionic liquids, as used hereinafter, refer to the complex of mixtures where the ionic liquid comprises an organic cation and an anionic compound where the anionic compound is usually an inorganic anion. Although these catalysts can be very active, with alkylation reactions it is required to run the reactions at low temperatures, typically between −10° C. to 0° C., to maximize the alkylate quality. This requires cooling the reactor and reactor feeds, and adds substantial cost in the form of additional equipment and energy for using ionic liquids in the alkylation process. The most common ionic liquid catalyst precursors for the alkylation application include imidazolium, or pyridinium-based cations coupled with the chloroaluminate anion ($Al_2Cl_7^-$).

The anionic component of the ionic liquid generally comprises a haloaluminate of the form $Al_nX_{3n+1}$, where n is from 1 to 5. The most common halogen, X, is chlorine, or Cl. The ionic liquid mixture can comprise a mix of the haloaluminates where n is 1 or 2, and include small amount of the haloaluminates with n equal to 3 or greater. When water enters the reaction, whether brought in with a feed, or otherwise, there can be a shift, where the haloaluminate forms a hydroxide complex, or instead of $Al_nX_{3n+1}$, $Al_nX_m(OH)_x$ is formed where m+x=3n+1. An advantage of ionic liquids (IL) for use as a catalyst is the tolerance for some moisture. In contrast, solid catalysts used in alkylation generally are rapidly deactivated by the presence of water. Ionic liquids also present some advantages over other liquid alkylation catalysts, such as being less corrosive than catalysts like HF, and being non-volatile.

It has been found that alkylation reactions using some phosphonium based ionic liquids give high octane products when carried out at temperatures above or near ambient temperature. This provides for an operation that can substantially save on cost by removing refrigeration equipment from the process. The present invention provides a process for the alkylation of paraffins using a phosphonium based ionic liquid. The process of the present invention can be run at room temperature or above in an alkylation reactor to generate an alkylate product stream with high octane. The process includes passing a paraffin having from 2 to 10 carbon atoms to an alkylation reactor, and in particular an isoparaffin having from 4 to 10 carbon atoms to the alkylation reactor. An olefin having from 2 to 10 carbon atoms is passed to the alkylation reactor. The olefin and isoparaffin are reacted in the presence of an ionic liquid catalyst and at reaction conditions to generate an alkylate. The ionic liquid catalyst is a phosphonium based haloaluminate ionic liquid coupled with a Brønsted acid co-catalyst selected from the group consisting of HF, HCl, HBr, HI and mixtures thereof.

Ionic liquids found to work include phosphonium based ionic liquids selected from the group consisting of trihexyltetradecyl phosphonium-$Al_2X_7$, tributyl-hexylphosphonium-$Al_2X_7$, tripropylhexylphosphonium-$Al_2X_7$, tributylmethylphosphonium-$Al_2X_7$, tributylpentylphosphonium-$Al_2X_7$, tributylheptylphosphonium-$Al_2X_7$, tributyloctylphosphonium-$Al_2X_7$, tributylnonylphosphonium-$Al_2X_7$, tributyldecylphosphonium-$Al_2X_7$, tributylundecylphosphonium-$Al_2X_7$, tributyldodecylphosphonium-$Al_2X_7$, tributyltetradecylphosphonium-$Al_2X_7$, and mixtures thereof. X comprises a halogen ion selected from the group consisting of F, Cl, Br, I and mixtures thereof. A preferred ionic liquid is tri-n-butyl-hexylphosphonium-$Al_2X_7$, where the preferred halogen, X, is selected from Cl, Br, I, and mixtures thereof. Another preferred ionic liquid is tributylpentylphosphonium-$Al_2X_7$, wherein X comprises a halogen ion selected from the group consisting of Cl, Br, I, and mixtures thereof. Another preferred ionic liquid is tributyloctylphosphonium $Al_2X_7$, wherein X comprises a halogen ion selected from the group consisting of Cl, Br, I and mixtures thereof. In particular, the most common halogen, X, used is Cl.

The specific examples of ionic liquids in the present invention use phosphonium based ionic liquids mixed with aluminum chloride. The acidity needs to be controlled to provide for suitable alkylation conditions. The ionic liquid is generally prepared to a full acid strength with balancing through the presence of a co-catalyst, such as a Brønsted acid. HCl or any Brønsted acid may be employed as co-catalyst to enhance the activity of the catalyst by boosting the overall acidity of the ionic liquid-based catalyst.

The reaction conditions include a temperature greater than 0° C. with a preferred temperature greater than 20° C. Ionic liquids can also solidify at moderately high temperatures, and therefore it is preferred to have an ionic liquid that maintains its liquid state through a reasonable temperature span. A preferred reaction operating condition includes a temperature greater than or equal to 20° C. and less than or equal to 70° C. A more preferred operating range includes a temperature greater than or equal to 20° C. and less than or equal to 50° C.

Due to the low solubility of hydrocarbons in ionic liquids, olefins-isoparaffins alkylation, like most reactions in ionic liquids is generally biphasic and takes place at the interface in the liquid state. The catalytic alkylation reaction is generally carried out in a liquid hydrocarbon phase, in a batch system, a semi-batch system or a continuous system using one reaction stage as is usual for aliphatic alkylation. The isoparaffin and olefin can be introduced separately or as a mixture. The molar ratio between the isoparaffin and the olefin is in the range 1 to 100, for example, advantageously in the range 2 to 50, preferably in the range 2 to 20.

In a semi-batch system the isoparaffin is introduced first then the olefin, or a mixture of isoparaffin and olefin. The catalyst is measured in the reactor with respect to the amount of olefins, with a catalyst to olefin weight ratio between 0.1 and 10, and preferably between 0.2 and 5, and more preferably between 0.5 and 2. Vigorous stirring is desirable to ensure good contact between the reactants and the catalyst. The reaction temperature can be in the range 0° C. to 100° C., preferably in the range 20° C. to 70° C. The pressure can be in the range from atmospheric pressure to 8000 kPa, preferably sufficient to keep the reactants in the liquid phase. Residence time of reactants in the vessel is in the range of a few seconds to hours, preferably 0.5 min to 60 min. The heat generated by the reaction can be eliminated using any of the means known to the skilled person. At the reactor outlet, the hydrocarbon phase is separated from the ionic liquid phase by gravity settling based on density differences, or by other separation techniques known to those skilled in the art. Then the hydrocarbons are separated by distillation and the starting isoparaffin which has not been converted is recycled to the reactor.

Typical alkylation conditions may include a catalyst volume in the reactor of from 1 vol % to 50 vol %, a temperature of from 0° C. to 100° C., a pressure of from 300 kPa to 2500 kPa, an isobutane to olefin molar ratio of from 2 to 20 and a residence time of 5 min to 1 hour.

The paraffin used in the alkylation process preferably comprises an isoparaffin having from 4 to 8 carbon atoms, and more preferably having from 4 to 5 carbon atoms. The olefin used in the alkylation process preferably has from 3 to 8 carbon atoms, and more preferably from 3 to 5 carbon atoms. One of the objectives is to upgrade low value C4 hydrocarbons to higher value alkylates. To that extent, one specific embodiment is the alkylation of butanes with butylenes to generate C8 compounds. Preferred products include trimethylpentane (TMP), and while other C8 isomers are produced, one competing isomer is dimethylhexane (DMH). The quality of the product stream can be measured in the ratio of TMP to DMH, with a high ratio desired.

In another embodiment, the invention comprises passing an isoparaffin and an olefin to an alkylation reactor, where the alkylation reactor includes an ionic liquid catalyst to react the olefin with the isoparaffin to generate an alkylate. The isoparaffin has from 4 to 10 carbon atoms, and the olefin has from 2 to 10 carbon atoms. The ionic liquid catalyst comprises a phosphonium based ionic liquid which is a quaternary phosphonium haloaluminate. The ionic liquid has a structure of the form $PR1R2R3R4-Al_2X_7$, where P refers to the phosphonium cation part of the ionic liquid, R1, R2, R3, and R4 are alkyl groups having between 4 and 12 carbon atoms, and X is a halogen from the group F, Cl, Br, I, and mixtures thereof.

The structure further includes that the R1, R2 and R3 alkyl groups are the same alkyl group, and the R4 comprises a different alkyl group, wherein the R4 group is larger than the R1 group, and that HR4 has a boiling point of at least 30° C. greater than the boiling point of HR1, at atmospheric pressure.

In one embodiment, R1, R2 and R3 comprise an alkyl group having from 3 to 6 carbon atoms, with a preferred structure of R1, R2 and R3 having 4 carbon atoms. In this embodiment, the R4 group comprises an alkyl group having between 5 and 8 carbon atoms, with a preferred structure of R4 having 6 carbon atoms. In this embodiment, the preferred quaternary phosphonium halide complex is tributylhexylphosphonium-$Al_2Cl_7$.

In another embodiment, the invention comprises passing an isoparaffin and an olefin to an alkylation reactor, where the alkylation reactor includes an ionic liquid catalyst to react the olefin with the isoparaffin to generate an alkylate. The isoparaffin has from 4 to 10 carbon atoms, and the olefin has from 2 to 10 carbon atoms. The ionic liquid catalyst comprises a phosphonium based ionic liquid which is a quaternary phosphonium haloaluminate. The ionic liquid has a structure of the form $PR1R2R3R4-Al_2X_7$, where P refers to the phosphonium cation of the ionic liquid, and R1, R2, R3, and R4 are alkyl groups having between 4 and 12 carbon atoms. The structure further includes that the R1, R2 and R3 alkyl groups are the same alkyl group, and the R4 comprises a different alkyl group, wherein the R4 group is larger than the R1 group, and that R4 has at least 1 more carbon atoms than the R1 group.

EXAMPLES

Example 1

Preparation of Tributyldodecyl Phosphonium Chloroaluminate Ionic Liquid

Tributyldodecyl phosphonium chloroaluminate is a room temperature ionic liquid prepared by mixing anhydrous tributyldodecyl phosphonium chloride with slow addition of 2 moles of anhydrous aluminum chloride per mole in an inert atmosphere. After several hours of mixing, a pale yellow liquid is obtained. The resulting acidic IL was used as the catalyst for the alkylation of isobutane with 2-butenes.

Example 2

Alkylation of Isobutane with 2-Butene Using Tributyldodecylphosphonium-$Al_2Cl_7$ Ionic Liquid Catalyst Alkylation of isobutane with 2-butene was carried out in a 300 cc continuously stirred autoclave. 8 grams of tributyldodecylphosphonium (TBDDP)-$Al_2Cl_7$ ionic liquid and 80 grams of isobutane were charged into the autoclave in a glovebox to avoid exposure to moisture. The autoclave was then connected to the plant and pressured to 500 psig using nitrogen. Stirring was started at 1900 rpm. 8 grams of olefin feed (2-butene feed to which 10% wt n-pentane tracer had been added) was then charged into the autoclave at an olefin space velocity of 0.5 g olefin/g IL/hr until the targeted i/o molar ratio of 10:1 was reached. Stirring was stopped and the ionic liquid and hydrocarbon phases were allowed to settle for 30 seconds. (Actual separation was almost instantaneous). The hydrocarbon phase was then analyzed by GC. For this example, the autoclave temperature was maintained at 25° C.

TABLE 1

| Alkylation with TBDDP-$Al_2Cl_7$ Ionic Liquid Catalyst | |
|---|---|
| Olefin Conversion, wt % | 100.0 |
| $C_5$+ Yield, wt. alkylate/wt olefin | 2.25 |
| $C_5$+ Alkylate RON-C | 95.7 |
| $C_5$-$C_7$ Selectivity, wt % | 15 |
| $C_8$ Selectivity, wt % | 77 |
| $C_9$+ Selectivity, wt % | 8 |
| TMP/DMH | 13.7 |

Examples 3-30

The procedure of Example 2 was repeated with a series of different phosphonium chloroaluminate ionic liquid catalysts at 25° C. (Table 2), 38° C. (Table 3), and 50° C. (Table 4). Four imidazolium or pyridinium ionic liquids were included to show the performance differences between phosphonium-based and nitrogen-based ionic liquids. The ionic liquids were: A—Tributyl dodecyl phosphonium-$Al_2Cl_7$, B—Tributyl decyl phosphonium-$Al_2Cl_7$, C—Tributyl octyl phosphonium-$Al_2Cl_7$, D—Tributyl hexyl phosphonium-$Al_2Cl_7$, E—Tributyl pentyl phosphonium-$Al_2Cl_7$, F—Tributyl methyl phosphonium-$Al_2Cl_7$, G—Tripropyl hexyl phosphonium-$Al_2Cl_7$, H—Butyl methyl imidazolium-$Al_2Cl_7$, I—Octyl methyl imidazolium-$Al_2Cl_7$, J—Butyl pyridinium-$Al_2Cl_7$, and K—Hexadecyl pyridinium-$Al_2Cl_7$.

TABLE 2

| Experimental Runs at 25° C. | | | | | | | | | | | |
|---|---|---|---|---|---|---|---|---|---|---|---|
| Example | 2 | 3 | 4 | 5 | 6 | 7 | 8 | 9 | 10 | 11 | 12 |
| Ionic Liquid | A | B | C | D | E | F | G | H | I | J | K |
| IL Cation | TBDDP | TBDP | TBOP | TBHP | TBPP | TBMP | TPHP | BMIM | OMIM | BPy | HDPy |
| Butene-Conversion, wt % | 100 | 100 | 100 | 100 | 100 | 100 | 100 | 100 | 100 | 100 | 100 |
| Isobutane/Olefin ratio, molar | 10.3 | 9.5 | 10.6 | 10.4 | 11.1 | 10.3 | 9.6 | 9.1 | 11.2 | 11.2 | 10.4 |
| IL/Olefin ratio, wt/wt | 1.07 | 0.98 | 1.10 | 1.07 | 1.15 | 1.09 | 0.99 | 0.94 | 1.16 | 1.18 | 1.07 |
| Temperature, ° C. | 25 | 25 | 25 | 25 | 25 | 25 | 25 | 25 | 25 | 25 | 25 |
| Pressure, psig | 500 | 500 | 500 | 500 | 500 | 500 | 500 | 500 | 500 | 500 | 500 |
| C5+ Alkylate Yield, w/w olefin | 2.25 | 2.08 | 2.13 | 2.13 | 2.20 | 2.00 | 2.18 | 2.01 | 2.08 | 2.10 | 2.17 |
| C5+ Product Selectivity, wt % | | | | | | | | | | | |
| C5-C7 | 15 | 12 | 11 | 10 | 8 | 10 | 14 | 10 | 14 | 10 | 20 |
| C8 | 77 | 80 | 82 | 84 | 87 | 85 | 78 | 83 | 79 | 84 | 69 |
| C9+ | 8 | 8 | 7 | 6 | 5 | 5 | 8 | 7 | 7 | 6 | 11 |
| TMP/DMH | 13.7 | 17.3 | 22.6 | 18.0 | 25.4 | 10.6 | 8.2 | 8.4 | 7.7 | 7.5 | 10.8 |
| C5+ Alkylate RON-C | 95.7 | 96.5 | 97.5 | 97.2 | 98.4 | 96.1 | 94.4 | 94.9 | 94.3 | 94.6 | 93.6 |

TABLE 3

Experimental Runs at 38° C.

| Example | 13 | 14 | 15 | 16 | 17 | 18 | 19 | 20 |
|---|---|---|---|---|---|---|---|---|
| Ionic Liquid | A | C | D | E | F | H | J | K |
| IL Cation | TBDDP | TBOP | TBHP | TBPP | TBMP | BMIM | BPy | HDPy |
| Butene-Conversion, wt % | 100 | 100 | 100 | 100 | 100 | 100 | 100 | 100 |
| Isobutane/Olefin ratio, molar | 8.8 | 9.0 | 10.4 | 10.1 | 10.5 | 8.8 | 11.7 | 11.8 |
| IL/Olefin ratio, wt/wt | 0.91 | 0.94 | 1.10 | 0.97 | 1.06 | 0.92 | 1.21 | 1.23 |
| Temperature, ° C. | 38 | 38 | 38 | 38 | 38 | 38 | 38 | 38 |
| Pressure, psig | 500 | 500 | 500 | 500 | 500 | 500 | 500 | 500 |
| C5+ Alkylate Yield, w/w olefin | 2.20 | 2.14 | 2.07 | 2.06 | 2.03 | 2.18 | 2.10 | 2.18 |
| C5+ Product Selectivity, wt % | | | | | | | | |
| C5-C7 | 29 | 16 | 12 | 15 | 16 | 16 | 13 | 24 |
| C8 | 61 | 76 | 81 | 74 | 75 | 76 | 87 | 64 |
| C9+ | 10 | 8 | 7 | 11 | 9 | 8 | 10 | 12 |
| TMP/DMH | 7.6 | 7.4 | 15.3 | 19.4 | 5.5 | 4.9 | 5.4 | 7.2 |
| C5+ Alkylate RON-C | 93.2 | 93.8 | 96.6 | 96.2 | 92.3 | 91.6 | 92.5 | 92.1 |

TABLE 4

Experimental Runs at 50° C.

| Example | 21 | 22 | 23 | 24 | 25 | 26 | 27 | 28 | 29 | 30 |
|---|---|---|---|---|---|---|---|---|---|---|
| Ionic Liquid | A | C | D | E | F | G | H | I | J | K |
| IL Cation | TBDDP | TBOP | TBHP | TBPP | TBMP | TPHP | BMIM | OMIM | BPy | HDPy |
| Butene-Conversion, wt % | 100 | 100 | 100 | 100 | 100 | 100 | 100 | 100 | 99 | 100 |
| Isobutane/Olefin ratio, molar | 8.6 | 11.5 | 10.5 | 15.0 | 9.6 | 8.8 | 9.4 | 9.5 | 10.8 | 10.0 |
| IL/Olefin ratio, wt/wt | 0.9 | 1.06 | 1.09 | 1.55 | 1.01 | 0.91 | 0.97 | 0.96 | 1.11 | 1.04 |
| Temperature, ° C. | 50 | 50 | 50 | 50 | 50 | 50 | 50 | 50 | 50 | 50 |
| Pressure, psig | 500 | 500 | 500 | 500 | 500 | 500 | 500 | 500 | 500 | 500 |
| C5+ Alkylate Yield, w/w olefin | 2.22 | 2.09 | 2.08 | 2.09 | 2.22 | 2.23 | 2.11 | 2.13 | 2.03 | 2.14 |
| C5+ Product Selectivity, wt % | | | | | | | | | | |
| C5-C7 | 25 | 21 | 16 | 15 | 25 | 28 | 22 | 43 | 18 | 26 |
| C8 | 63 | 69 | 76 | 77 | 65 | 59 | 68 | 43 | 73 | 61 |
| C9+ | 12 | 10 | 8 | 8 | 11 | 13 | 10 | 14 | 9 | 13 |
| TMP/DMH | 5.0 | 4.8 | 8.5 | 7.0 | 3.5 | 3.5 | 3.1 | 1.3 | 3.8 | 4.5 |
| C5+ Alkylate RON-C | 90.8 | 91.2 | 94.4 | 93.7 | 88.7 | 88.2 | 87.8 | 82.4 | 89.4 | 90.1 |

Figure 2:
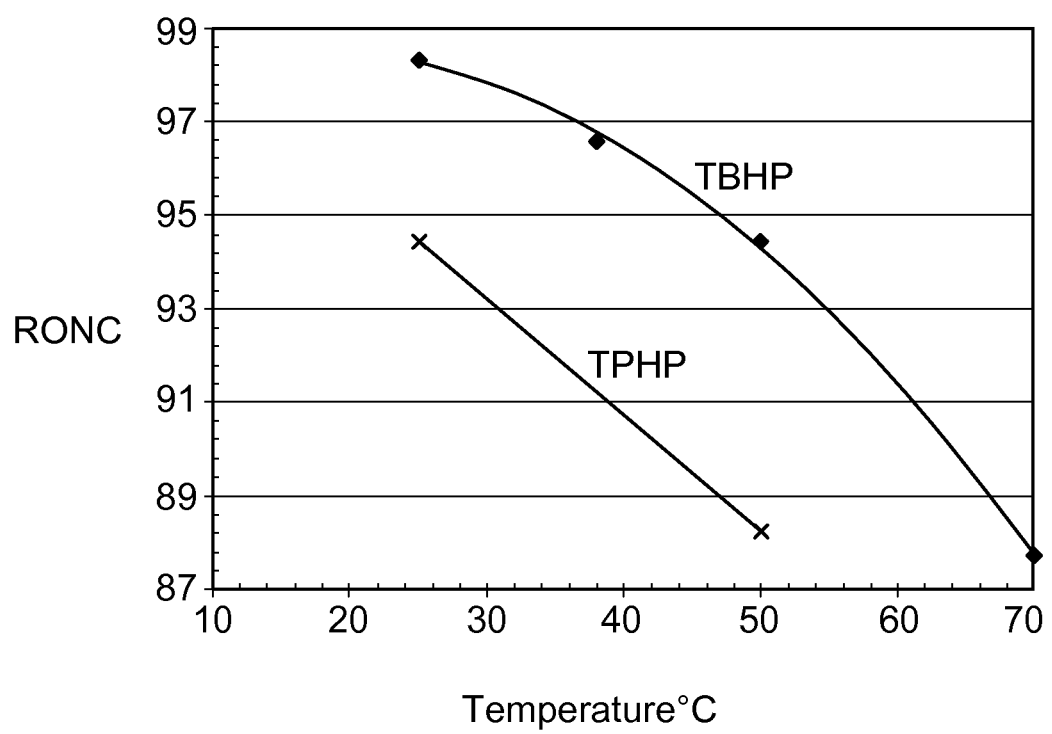
FIG. 2 shows the effect of symmetric side chain length on alkylation performance of phosphonium chloroaluminate ionic liquids.

Based on screening this series of phosphonium-based chloroaluminate ionic liquids, we have discovered a good candidate capable of producing high octane alkylate even when run at 50° C. As shown in FIG. 1, being able to design the ionic liquid with an appropriate carbon chain length has an impact on the product quality. FIG. 1 shows the optimized octane as a function of temperature for different chloroaluminate ionic liquids. The figure shows the results for TBMP-1 (tributylmethylphosphonium chloroaluminate), TBPP-5 (tributylpentylphosphonium chloroaluminate), TBHP-6 (tributylhexylphosphonium chloroaluminate), TBOP-8 (tributyloctylphosphonium chloroaluminate), TBDP-10 (tributyldecylphosphonium chloroaluminate), and TBDDP-12 (tributyldodecylphosphonium chloroaluminate). The optimum length of the asymmetric side-chain ($R_4$ in $PR_1R_2R_3R_4$—$Al_2Cl_7$, where $R_1$=$R_2$=$R_3 \neq R_4$) is in the 5 or 6 carbon number range. Note that if there is not at least one asymmetric side chain, the ionic liquid could easily crystallize and not remain a liquid in the temperature range of interest. If the asymmetric chain is too long, it is subject to isomerization and cracking. FIG. 2 shows the drop in performance when the size of symmetric side chain ($R_1$=$R_2$=$R_3$) is reduced from $C_4$ to $C_3$. FIG. 2 is a plot of the optimized octane as a function of temperature for different chloroaluminate ionic liquids, showing TPHP (tripropylhexylphosphonium chloroaluminate) and TBHP (tributylhexylphosphonium chloroaluminate). Without being bound by theory, it appears that the butyl side chains provide for better association and solubility with the isobutane and butene feed components and that this may help to maintain a high local i/o at the active site.

Figure 3:
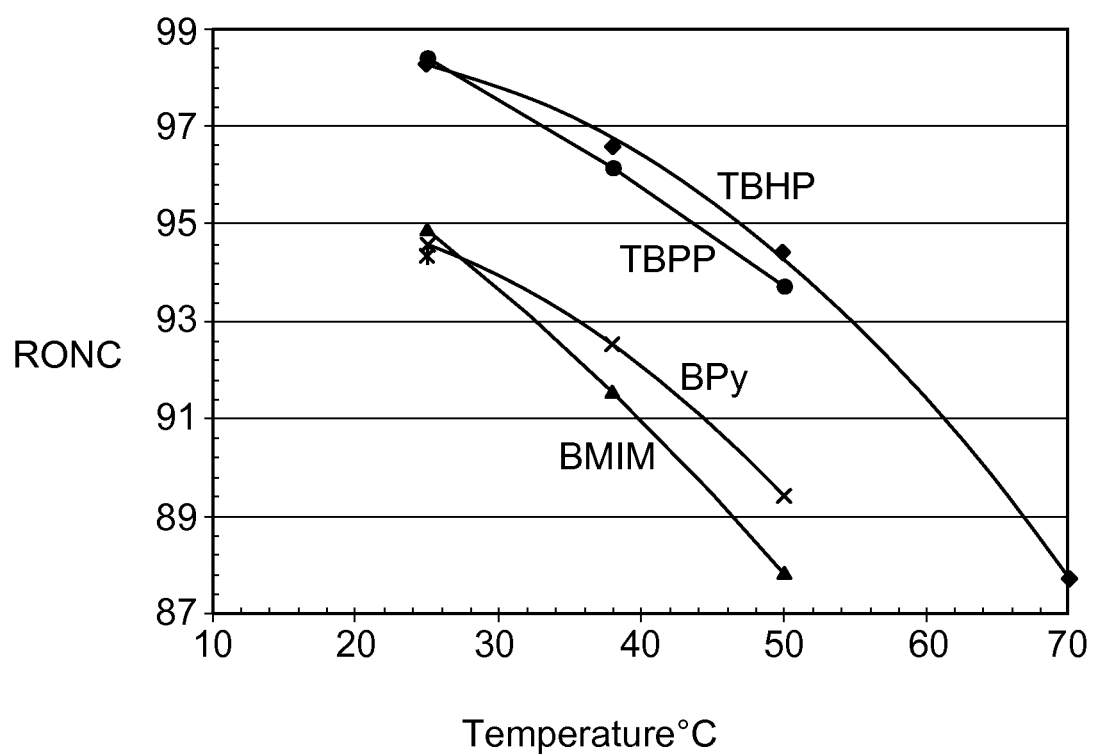
FIG. 3 shows a comparison of the alkylation performance of phosphonium-based and nitrogen-based chloroaluminate ionic liquids.
Figure 4:
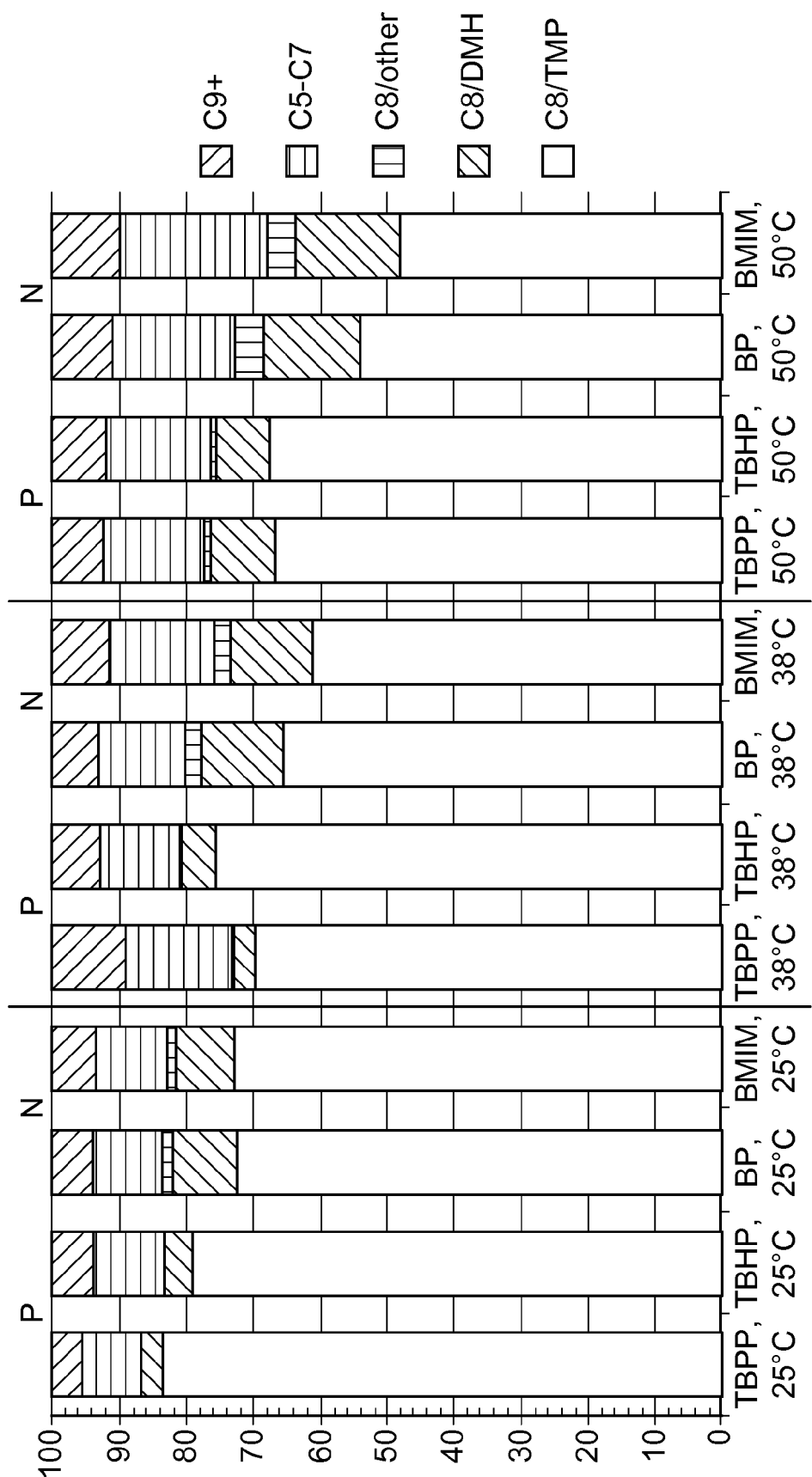
FIG. 4 shows the effect of temperature on product selectivity for phosphorous-based versus nitrogen-based chloroaluminate ionic liquids.

FIGS. 3 and 4 compare the performance of the better phosphonium-chloroaluminate ionic liquids with several nitrogen-based ionic liquids, including 1-butyl 3-methyl imidazolium (BMIM) chloroaluminate and butyl pyridinium (BPy) chloroaluminate, which have been widely used and reported in the literature. FIG. 3 shows the optimized octane as a function of temperature for the ionic liquids TBHP (tributylhexylphosphonium chloroaluminate), TBPP (tributylpentylphosphonium chloroaluminate), BPy (butyl pyridinium chloroaluminate), and BMIM (butyl-methyl-imidazolium chloroaluminate). FIG. 4 shows the difference in product selectivities for P-based versus N-based chloroaluminate ionic liquids. The phosphonium-based ionic liquids gave consistently better TMP to DMH ratios and better Research Octane numbers than the nitrogen-based ionic liquids. Whereas the alkylate RONC dropped off below 90 for the nitrogen-based ionic liquids as the temperature was increased to 50° C., the phosphonium-based ionic liquids were still able to provide a Research Octane Number of ~95. This provides an economic advantage when designing the alkylation unit in that expensive refrigeration equipment is not needed, and/or the unit can be operated at lower i/o ratio for a given product quality.

While the invention has been described with what are presently considered the preferred embodiments, it is to be understood that the invention is not limited to the disclosed embodiments, but it is intended to cover various modifications and equivalent arrangements included within the scope of the appended claims.

The invention claimed is:

1. A process for the alkylation of isoparaffins comprising:
   passing an isoparaffin having from 4 to 10 carbon atoms to an alkylation reactor; and
   passing an olefin having from 2 to 10 carbon atoms to the alkylation reactor, wherein the alkylation reactor is operated at reaction conditions and has an unsupported phosphonium based ionic liquid catalyst and a Brønsted acid selected from the group consisting of HCl, HBr, HI, HF and mixtures thereof, for reacting the olefin and the isoparaffin to generate an alkylate, wherein the phosphonium based ionid liquid has a structure of the form PR1R2R3R4-$Al_2X_7$, wherein P refers to the phosphonium cation part of the ionic liquid, X refers to a halogen atom, R1, R2, R3 and R4 are alkyl groups having between 4 and 12 carbon atoms, and that the R1, R2 and R3 alkyl groups are the same alkyl group, and the R4 alkyl group comprises a different alkyl group than the R1, R2 and R3 alkyl groups, wherein the R4 alkyl group contains more carbon atoms than the R1, R2 and R3 alkyl groups, wherein the volume fraction of the phosphonium based ionic liquid catalyst is less than 30% of a reaction mixture, and wherein the reaction mixture refers to a mixture of the phosphonium based ionic liquid catalyst and hydrocarbons contained in the alkylation reactor.

2. The process of claim 1, wherein the phosphonium based ionic liquid catalyst is selected from the group consisting of tributyl-hexylphosphonium-$Al_2X_7$, tripropylhexylphosphonium-$Al_2X_7$, tributylpentylphosphonium-$Al_2X_7$, tributylheptylphosphonium-$Al_2X_7$, tributyloctylphosphonium-$Al_2X_7$, tributylnonylphosphonium-$Al_2X_7$, tributyldecylphosphonium-$Al_2X_7$, tributylundecylphosphonium-$Al_2X_7$, tributyldodecylphosphonium-$Al_2X_7$, tributyltetradecylphosphonium-$Al_2X_7$, and mixtures thereof, wherein X comprises a halogen ion selected from the group consisting of F, Cl, Br, I and mixtures thereof.

3. The process of claim 2, wherein the phosphonium based ionic liquid catalyst is tri-n-butyl-hexylphosphonium-$Al_2X_7$, tributylpentylphosphonium-$Al_2X_7$, tributylheptylphosphonium-$Al_2X_7$, tributyloctylphosphonium-$Al_2X_7$, wherein X comprises a halogen atom selected from the group consisting of Cl, Br, I and mixtures thereof.

4. The process of claim 3, wherein the phosphonium based ionic liquid catalyst is tri-n-butyl-hexylphosphonium-$Al_2X_7$ or tributylpentylphosphonium-$Al_2X_7$, wherein X comprises a halogen atom selected from the group consisting of Cl, Br, I, and mixtures thereof.

5. The process of claim 2, wherein the phosphonium based ionic liquid catalyst is tributylpentylphosphonium-$Al_2X_7$, wherein X comprises a halogen atom selected from the group consisting of Cl, Br, I and mixtures thereof.

6. The process of claim 2, wherein the phosphonium based ionic liquid catalyst is tributylhexylphosphonium-$Al_2X_7$, wherein X comprises a halogen atom selected from the group consisting of Cl, Br, I and mixtures thereof.

7. The process of claim 1, wherein the reaction conditions include a reaction temperature greater than 0° C.

8. The process of claim 7, wherein the reaction conditions include a reaction temperature greater than or equal to 20° C.

9. The process of claim 7, wherein the reaction conditions include a reaction temperature greater than or equal to 20° C., and less than or equal to 70° C.

10. The process of claim 1, wherein the isoparaffin has from 4 to 8 carbon atoms.

11. The process of claim 10, wherein the isoparaffin has from 4 to 5 carbon atoms.

12. The process of claim 1, wherein the olefin has from 3 to 8 carbon atoms.

13. The process of claim 12, wherein the olefin has from 3 to 5 carbon atoms.

14. A process for the alkylation of isoparaffins comprising:
   passing an isoparaffin having from 4 to 6 carbon atoms to an alkylation reactor; and
   passing an olefin having from 2 to 6 carbon atoms to the alkylation reactor, wherein the alkylation reactor is operated at reaction conditions and has an unsupported phosphonium based ionic liquid catalyst and a Brønsted acid for reacting the olefin and the isoparaffin, wherein the phosphonium based ionic liquid catalyst is selected from the group consisting of tri-n-butyl-hexylphosphonium-$Al_2X_7$, trihexyl-tetradecylphosphonium-$Al_2X_7$, tripropylhexylphosphonium-$Al_2X_7$, tributylpentylphosphonium-$Al_2X_7$, tributylheptylphosphonium-$Al_2X_7$, tributyloctylphosphonium-$Al_2X_7$, tributylnonylphosphonium-$Al_2X_7$, tributyldecylphosphonium-$Al_2X_7$, tributyldodecylphosphonium-$Al_2X_7$, tributyltetradecylphosphonium-$Al_2X_7$, and mixtures thereof, and wherein X comprises a halogen atom selected from the group consisting of F, Cl, Br, I, and mixtures thereof, and the reaction conditions include a reaction temperature greater than 0° C., wherein the volume fraction of the phosphonium based ionic liquid catalyst is less than 30% of a reaction mixture, and wherein the reaction mixture refers to a mixture of the ionic liquid catalyst and hydrocarbons contained in the alkylation reactor.

15. The process of claim 14, wherein the isoparaffin has from 4 to 5 carbon atoms.

16. The process of claim 14, wherein the olefin has from 3 to 5 carbon atoms.

17. The process of claim 14, wherein the isoparaffin is isobutane and the olefin is a mixture of butenes.

18. A process for the alkylation of isoparaffins comprising:
   passing an isoparaffin having from 4 to 10 carbon atoms to an alkylation reactor; and
   passing an olefin having from 2 to 10 carbon atoms to the alkylation reactor, wherein the alkylation reactor is operated at reaction conditions and has an unsupported phosphonium based ionic liquid catalyst and a Brønsted acid selected from the group consisting of HCl, HBr, HI, HF and mixtures thereof, for reacting the olefin and the isoparaffins to generate an alkylate, wherein the phosphonium based ionic liquid catalyst has a structure of the form PR1R2R3R4-$Al_2X_7$, wherein P refers to the phosphonium cation part of the ionic liquid, X refers to a halogen atom, R1, R2, and R3 are the same alkyl group having 4 carbon atoms, and that the R4 comprises a different alkyl group than the R1, R2 and R3 alkyl groups having 5 or 6 carbon atoms, wherein the volume fraction of the phosphonium based ionic liquid catalyst is less than 30% of a reaction mixture, and wherein the reaction mixture refers to a mixture of the phosphonium based ionic liquid catalyst and hydrocarbons contained in the alkylation reactor.

19. The process of claim 18, wherein the isoparaffin has from 4 to 5 carbon atoms.

20. The process of claim 18, wherein the olefin has from 3 to 5 carbon atoms.

* * * * *